United States Patent [19]

Pecht et al.

[11] Patent Number: 4,683,135
[45] Date of Patent: Jul. 28, 1987

[54] DSCG BINDING PROTEIN AND PROCESS FOR PREPARING SAME

[75] Inventors: Israel Pecht, Rehovot; Nachman Mazurek, Raanana, both of Israel

[73] Assignee: Yeda Research and Development Co., Ltd., Rehovot, Israel

[21] Appl. No.: 843,912

[22] Filed: Mar. 20, 1986

Related U.S. Application Data

[63] Continuation of Ser. No. 517,843, Jul. 27, 1983, abandoned.

[51] Int. Cl.[4] .......................... C07K 15/06; C07K 3/28
[52] U.S. Cl. .......................................... 424/85; 424/88; 435/68; 435/240; 435/241; 530/350; 530/363; 530/387; 530/405; 530/406; 530/409; 530/410; 530/413; 530/809; 530/828
[58] Field of Search ............... 260/112 R; 424/85, 88; 435/68, 240, 241; 530/350, 406, 410, 413, 363, 405, 409, 809, 828, 387

[56] References Cited

U.S. PATENT DOCUMENTS 4,340,581  7/1982  Timpl .......................... 260/112 R X

OTHER PUBLICATIONS

Chem. Abstracts, vol. 94, 1981, 10835f, Mazurek et al.
Chem. Abstracts, vol. 97, 1982, 122337p, Mazurek et al.
Nature, vol. 286, 1980, pp. 722–723, Mazurek et al.
EMBO Journal, vol. 1, No. 5, Jul. 28, 1982, Mazurek et al, pp. 585–590.

*Primary Examiner*—Howard E. Schain
*Attorney, Agent, or Firm*—Browdy and Neimark

[57]  ABSTRACT

According to the present invention there is provided an essentially pure protein found in nature in mast cells and in basophiles, which protein is involved in the transfer of calcium into such cells. Such a protein has an isoelectric point of about 3.9 and a MW about $60,000 \pm 2,000$, and has an amino acid composition as herein defined. There are also provided processes for the preparation of such purified protein. Such protein is of use in blocking histamine release from cells.

15 Claims, 2 Drawing Figures

DSCG BINDING PROTEIN AND PROCESS FOR PREPARING SAME

This application is a continuation of application Ser. No. 517,843 filed 7/27/83, now abandoned.

BACKGROUND OF THE INVENTION

It has been known for some time that the anti-allergic drug, disodium salt of 1,2 bis(-2 carboxychromon-5-yloxy)-2-hydroxy propane, is effective in the treatment of allergic brochial asthma and related symptoms. It has been shown that specific binding of that drug occurs to mast cells and basophile external membranes in a $Ca^{2+}$ dependent manner. Furthermore, this binding is accompanied by the inhibition of degranulation of these cells and their secretion of vasoactive amines [Mazurek et al., Nature, 286, 722–723 (1980)].

SUMMARY OF THE INVENTION

The present invention relates to processes for the preparation of a chemically substantially pure membrane component of basophiles and mast cells capable of binding $Ca^{2+}$ ions and the anti-allergic drug, disodium salt of 1,2 bis(-2 carboxychromon-5-yloxy)-2-hydroxy propane, to the purified substance, to pharmacological preparations containing said purified substance as an ingredient, to pharmaceutical preparations containing reagents reacting specifically with this purified protein (like specific antibodies) and to other methods of treatment making use of said novel purified composition of matter.

In view of the recognition of the important and valuable properties of this cell membrane component in blocking allergic reactions, it was considered to be of significant value and advantage to obtain this in chemically pure form so as to make it possible to use it in medicine as well as in research. Only a purified substance can be employed in designing and production of reagents that could be developed for alternative more effective treatment of allergy by blocking that crucial element in the sequence of events leading to the release of mediators from mast cells or basophiles.

The membrane protein component present in basophile and mast cells, responsible for the specific, $Ca^{2+}$ dependent, binding of the anti-allergic drug Cromolyn [disodium cromoglycate, DSCG; the disodium salt of 1,2 bis(-2 carboxychromon-5-yloxy)-2-hydroxy propane] was isolated by three procedures, all based on affinity for the drug.

The apparent molecular weight of the protein is 60,000±2,000 based on polyacrylamide gel electrophoresis and its amino acid composition is: asparagine—4 units; threonine and serine—3 units; glutamine—3 units; glycine—2 units; alanine—2 units; proline—2 units; cysteine—1 unit; valine—2 units; methionine—1 unit; isoleucine—1 unit; leucine—2 units; tyrosine—1 unit; phenylalanine—1 unit; histamine—1 unit; lysine—2 units; arginine—1 unit.

The preparation process of that protein comprises either of the following procedures:

(1)

(a) Treatment of basophiles or mast cells with a covalent polyvalent conjugate of a protein (like bovine serum albumin) and the drug DSCG.
(b) Solubilization of the cells membrane with a non-ionic detergent (like NP-40).
(c) Precipitation from the lysates, by the subsequent addition to it of antibodies specific for the drug, or a single protein binding the drug.
(d) Separation of the components by gel electrophoresis.

(2)

(a) Solubilization of the membranes of basophiles or mast cells by a non-ionic detergent (like NP-40).
(b) Preparation of an affinity column by covalently conjugating the drug DSCG through its 2-hydroxy propane grouping to an insoluble matrix (like agarose).
(c) Absorption of the DSCG-binding protein from the cell lysate onto the affinity column.
(d) Specific elution of the DSCG binding protein from the column by the free drug or by a $Ca^{2+}$ chelating agent.

(3)

(a) Treatment of an acetone extract of basophiles or mast cells with a protein (like bovine serum alumin) covalently conjugated with both DSCG and a hapten (like 2,3 dinitrophenyl) groups.
(b) Absorption of the complexes formed on a column composed of a solid matrix derivatized with antibodies specific to the hapten.
(c) Elution of the drug-binding protein with free hapten or a $Ca^{2+}$ chelating agent.

By establishing the amino acid sequence, it is possible to prepare such protein synthetically by techniques conventional in protein chemistry.

The protein (CBP) can be used for controlling calcium flux and histamine release. It is possible to modify such protein and thus obtain substances which are adapted to block such allergic reactions or to alleviate same. The addition of such protein or its introduction into cell or cell membranes enhances calcium passage through such membranes.

Although herein the preparation of the membrane drug receptor is illustrated with reference to a rat basophilic leukemia cell line as a source, it is understood that it is by way of example only and that other similar sources of that protein can be used.

The processes according to the present invention comprise of the three different approaches all based on the $Ca^{2+}$ dependent affinity of the membrane protein to the drug. The product of all three approaches leads to one and the same material characterized by a single defined band of protein as analyzed by electrophoretic focusing and the enclosed amino acid analysis (Table I).

TABLE I

AMINO ACID COMPOSITION OF RBL-2H3 MEMBRANE RECEPTOR FOR DSCG

| | | |
|---|---|---|
| Asparagine | 1.79 | 3.69 |
| Threonine + Serine | 1.07 | 2.20 |
| Glutamine | 1.21 | 2.49 |
| Glycine | 0.93 | 1.91 |
| Alanine | 0.64 | 1.32 |
| Proline | 0.68 | 1.41 |
| Cysteine | 0.08 | 0.17 |
| Valine | 0.63 | 1.29 |
| Methionine | 0.19 | 0.39 |
| Isoleucine | 0.34 | 0.70 |
| Leucine | 1.00 | 2.06 |
| Tyrosine | 0.31 | 0.64 |
| Phenylalanine | 0.49 | 1.00 |
| Histamine | 0.24 | 0.50 |
| Lysine | 0.62 | 1.27 |

TABLE I-continued

AMINO ACID COMPOSITION
OF RBL-2H3 MEMBRANE RECEPTOR FOR DSCG

| Arginine | 0.38 | 0.78 |

(1) Isolation of the DSCG Binding Protein by Immunoprecipitation

Surface radioiodinated RBL-2H3 cells ($2 \times 10^\circ$/ml) were incubated with a multivalent DSCG-BSA conjugate in a buffer solution for 1 hour at 4° C. Unreacted DSCG-BSA was removed by several washings. Then, the cells were subjected to solubilization with a nonionic detergent (1% NP-40). Nonspecific, clearing precipitation was obtained by reacting one ml of the lysate with goat antilysozyme serum and lysozyme. Lysates were allowed to precipitate for 24 hours and later spun down at 13,000 g and the pellets discarded. The DSCG binding protein was subsequently precipitaed from those lysates with rabbit anti-DSCG antibodies and DSCG-BSA as a carrier. The immune precipitate formed was spun down and washed with PBS containing 0.1% NP-40. The washed precipitates were dissolved in SDS sample buffer and subjected to polyacrylamide gel electrophoresis. Only a single readioactive band, of 60,000 molecular weight, was observed (FIG. 1). The meracaptoethanol-reduced precipitate also yielded one band on PAGE, yet it was retarded relative to the unreduced protein, hence having an apparent molecular weight of 75,000 (FIG. 1).

(2) Isolation of the DSCG-Binding Protein by affinity chromatography

Affinity chromatography was performed on a column of DSCG coupled to polyacryhydrazido agarose (PAHA). Lysates of the surface iodinated RBL-2H3 cells were applied to the DSCG-coupled PAHA column and to a nonderivatized control column. The lysates were allowed to absorb for 24 hours. Later, the columns were washed with Tyrode containing NP-40, until no radioactivity could be detected in the washings. The columns were then eluted either with 10 mM DSCG in Tyrode containing NP-40 or with 10 mM EDTA. Significantly higher amounts of iodinated protein were eluted by EDTA or DSCG from the DSCG-substituted column compared with amount of iodinated protein eluted under the same conditions from the non-derivatized control column. This indicates the specificity of the eluted product for DSCG. The EDTA eluates were concentrated in ultra-thimbles, and a sample was applied to a SDS-PAGE. A single band of $60 \times 10^3$ daltons was observed migrating similarly to the immunoprecipitated protein (FIG. 1, lane F).

(3) Isolation by Immuno-affinity chromatography

An acetone extract of the RBL-2H3 tumor cells has been prepared according to the method of Hudgin et al., J. Biol. Chem., 243, 5536-5543 (1974). The powder has been suspended in phosphate buffer and the insoluble fraction sedimented by centrifugation. The pellet was again extracted by distilled water and blended in phosphate buffer containing triton X-100. Again, the extract was cleared by centrifugation, and this time the supernatant was recovered and used for the following steps. This includes passing through a Sepharose 6B column to remove non-specific adherent components. The eluate was reacted with the covalent conjugate of a protein (bovine serum albumin) with the hapten (DNP) and the drug (DSCG) and run through an affinity column for the hapten (Sepharose 6B derivatized with anti-DNP antibodies). Elution of the specific mebrane protein was achieved by either a $Ca^{2+}$ chelating agent (EDTA) or the free hapten (2,3 dinitrophenol) without any denaturing agent.

EXAMPLE 1

Isolation of the DSCG-binding Protein by Immunoprecipitation

Step A: Preparation of DSCG-BSA conjugate

Glutaraldehyde was used as a bifunctional reagent to couple the drug to BSA. For that end a derivative of DSCG with a spacer carrying a free amine (DSCG-NH$_2$) has been synthesized: An ether was formed between the -2-hydroxy group of DSCG and the alpha carbon of 1-sulfate-2-amino ethane. Twenty mg of DSCG were dissolved in 2 ml of 0.1 M Tris buffer pH 9.0 and slowly reacted with 0.2 M of 1-sulfate-2-amino ethane while stirring for four hours at room temperature. Upon acidification with 0.05 NHCl, a precipitate of the product has formed. This was thrice washed with water and dissolved upon adjusting the pH to 7.5 with NaOH.

Two hundred mg of BSA were dissolved in 8 ml of 0.05 M NaHCO$_3$. Ten ml of a 2.5% aqueous solution of glutaraldehyde were added with continous gentle stirring for 30 minutes at room temperature. Then 25 mg of DSCG-NH$_3$ were added and the reaction mixture was stirred for an additional 2 hours at room temperature. The Schiff base thus formed, was reduced with sodiumborohydride (0.5 mg/ml). This was followed by dialysis, with several changes, for 48 hours at 4° C. against distilled water. The resultant conjugate solution was turbid yet was used as such for immunizations. It was filtered through Millipore filters (0.45 μm) for all other purposes. The mean number of DSCG molecules coupled per molecule of BSA in the soluble (Millipore filtered) fraction of the conjugate, was determined by calculating the absorbancy ratio of the conjugated BSA at 280 and 232 nm, and was found to be 4-5 molecules of DSCG per molecule of BSA. In the turbid material used for immunization the content of DSCG was significantly higher.

Step B: Immunization

Rabbits were immunized by multisite intradermal injections of 2 mg DSCG-BSA/rabbit in complete Freund's adjuvant. Three weeks later they were boosted with 1 mg DSCG-BSA and were bled 4 and 5 weeks after immunization. The serum was separated and stored frozen.

Step C: Antisera

Specificity of rabbit anti-DSCG antibodies was checked by a precipitation titration of the immune serum with a range of DSCG-BSA concentrations. Both spectroscopic and radioimmune quantitation of the formed immunoprecitates showed a bell-shape dependence on antigen concentration. Upon competitive inhibition by excess of free DSCG more the 90% reduction in the amount of the immunoprecipite formed was achieved. No cross reaction of the anti-serum with BSA was detected. A similar immunoprecipitation was also formed when DSCG was conjugated to a different protein carrier—Keyhole limpet hemocyanin.

Step D: Tissue Culture

The rat basophilic leukemia cell line (RBL-2H3) was grown in Eagle's minimal essential medium (with Earle's salts), supplemented with 20% fetal calf serum, 1 mM glutamine, 200 I.U. penicillin/ml and 200 ug steptomycine/ml (supplied by Bio-Lab, Jerusalem). Cells were grown in 250 ml Nunc tissue culture T-flasks, at 37° C., in a humid, 5% $CO_2$ atmosphere incubator. Cells for the experiments were taken in the early stationary growth phase, 48 hours after transfer, and removed from the flask by means of a rubber policeman. They were washed thrice with Hank's balanced salt solution (HBSS) and then resuspended in that medium ($2 \times 10^7$ cells/ml) and subjected to cell surface iodination.

Step E: Cell Surface Radioiodination

Lactoperoxidase-catalyzed radioiodination of cell surface proteins was performed as described by Marchalonis [Biochem. J. 113, 299 (1969)] with 1 $mCi^{125}I$ on $(1.5-2) \times 10^7$ cells. Iodination was teminated by washing the cells three times in cold HBSS. Lysates were prepared by suspending the cells in PBS containing 0.5 M iodoacetamide, followed by the addition of an equal volume of 1% NP-40 in PBS, containing also $10^{-5}$ M phenyl methylsulfonyl fluoride (PMSF) and 1000 K.I.U./ml Trasylol, as proteolysis inhibitors. Nuclei were removed by centrifugation at 2000 g and the supernatant was dialyzed overnight at 4° C. against Tyrode buffer (137 mM NaCl, 2.7 mM KCl, 0.4 mM $NaH_2PO$, 10 mM HEPES, 1 mM MgCl, 5.6 mM glucose), with or without $Ca^{2+}$ (1.8 mM), containing $10^{-5}$ M PMSF and $2.5 \times 10^{-3}$ M iodoacetamide. The dialyzed lysates were centrifuged in a Sorvall RC2-B centrifuge using an SS-34 rotor and 30,000 g for 2 hours.

Step F: Isolation of the DSCG Binding Protein by Immunoprecipitation

Surface radioiodinated RBL-2H3 cells ($2 \times 10^7$/ml) were incubated with 40 μg of multivalent DSCG-BSA in a 0.5% BSA containing Tyrode solution for 1 hour at 4° C. Unreacted DSCG-BSA was removed by several washings. Then the cells were subjected to solubilization with a nonionic detergent (1% NP-40). Non-specific, clearing precipitation was obtained by reacting 1 ml of lysate with 200 μl of goat antilysozyme serum and 20 μg lysozyme. Lysates were allowed to precipitate for 24 hours at 4° C. and later spun down at 13,000 g and the pellets discarded. The DSCG binding protein was subsequently precipitated from those lysates (1 ml) with rabbit anti-DSCG antibodies (200 μg) and DSCG-BSA (40 μg) as a carrier. The immune precipitate formed over 48 hours at 4° C. was spun down (13,000 g) and washed 3 times with PBS containing 0.1% NP-40. The washed precipitates were dissolved in SDS sample buffer and subjected to polyacrylamide gel electrophoresis as described under Step G.

Obtained: Only a single radioactive band, of 60,000 molecular weight, was observed (FIG. 1, lane C). The mercaptoethanol-reduced precipitate also yielded one band on PAGE, yet it was retarded relative to the unreduced protein, hence having an apparent molecular weight of 75,000.

Step G: Polyacrylamide Gel Electrophoresis

Electrophoresis was performed in a discontinuous buffer system, according to Laemmli [Nature, 227, 680, (1970)]. Two mm thick slab gels with a linear concentration gradient of polyacrylamide between 7% and 20% were used. The following unlabeled proteins with the respective molecular weights were run on each gel as molecular weight markers. Phosphorylase B $94 \times 10^3$, BSA $67 \times 10^3$, ovalbumin $45 \times 10^3$, carbonic anhydrase $30 \times 10^3$, soybean trypsin inhibitor $20.2 \times 10^3$, lactalbumin $4.4 \times 10^3$. The sample buffer used to dissolve immunoprecipitates contained 3% sodium dodecyl sulfate, 0.625 M Tris-HCl buffer pH 8.0, 10% glycerol and 0.2% bromophenol blue, with or without 0.25 M mercaptoethanol. Gels were stained by Coomassie brilliant blue, dried and autoradiographed.

EXAMPLE 2

Isolation of the DSCG-Binding Protein by Affinity Chromatography

Step A: Affinity Column Preparation

Polyacrylhydrazido-agarose (PAHA) was used as a support for immobilization of DSCG. The affinity column was prepared according to the procedure described by Miron et al, [J. Solid Phase Biochem, 1, 115, (1976)]. The PAHA was derivatized with glutaraldehyde with slow stirring for 4 hours. The resin was then washed until no odor of glutaraldehyde could be detected. The washed glutaraldehyde-PAHA was suspended in three volumes of 0.1 M sodium phosphate buffer 7.5, containing 20 mg of the DSCG-$NH_3$. After slow stirring for 12 hours at 4° C. the DSCG-PAHA complex was washed with cold PBS. Reduction of the Schiff base was carried out in 1.5 volumes of PBS containing 0.5 mg/ml of $NaBH_4$ for 6 hours at 4° C. The non derivatized control column was rected with glutaraldehyde only and the former Schiff base, was reduced with sodium borohydride. Nonconjugated derivative of DSCG was determined spectrophotometrically in the supernatant after centrifugation. The amount of bound DSCG was calculated from the difference and found to be 15 mg DSCG/gm PAHA.

Step B: Tissue Culture

The rat basophilic leukemia cell line (RBL-2H3) was grown in Eagle's minimal essential medium (with Earle's salts), supplemented with 20% fetal calf serum, 1 mM glutamine, 200 I.U. penicillin/ml and 200 μg stepomycine/ml (supplied by Bio-Lab, Jerusalem). Cells were grown in 250 ml Nunc tissue culture T-flasks, at 37° C., in a humid, 5% $CO_2$ atmosphere incubator. Cells for the experiments were taken in the early stationary growth phase, 48 hours after transfer, and removed from the flask by means of a rubber policeman. They were washed thrice with Hank's balanced salt solution (HBSS) and then resuspended in that medium ($2 \times 10^7$ cells/ml) and subjected to cell surface iodination.

Step C: Cell Surface Radioiodination of Cell Surface Proteins

Lactoperoxidase-catalyzed radioiodination of cell surface proteins was performed as described by Marchalonis [Biochem. J., 113, 299 (1969)] with 1 $mCi^{125}I$ on $(1.5-2) \times 10^7$ cells. Iodination was terminated by washing the cells three times in cold HBSS. Lysates were prepared by suspending the cells in PBS containing 0.5 M iodoacetamide, followed by the addition of an equal volume of 1% NP-40 in PBS, containing also $10^{-5}$ M phenyl methylsulfonyl fluoride (PMSF) and 1000 K.I.U./ml Trasylol, as proteolysis inhibitors. Nuclei were removed by centrifugation at 2000 g and the supernatant was dialyzed overnight at 4° C. against Tyrode buffer (137 mM NaCl, 2.7 mM KCl, 0.4 mM $NaH_2PO$, 10 mM HEPES, 1 mM MgCl, 5.6 mM glucose), with or without $Ca^{2+}$ (1.8 mM), containing $10^{-5}$ M PMSF and $2.5 \times 10^{-3}$ M iodoacetamide. The dialyzed lysates were centrifuged in a Sorvall RC2-B centrifuge using an SS-34 rotor at 30,000 g for 2 hours.

Step D: Isolation of the DSCG-binding Protein by Affinity Chromatography

Affinity chromatography was performed on a 10 ml column of DSCG coupled to polyacryhydrazido agarose (PAHA). One ml of lysates of the surface iodinated RBL-2H3 cells ($2 \times 10^7$) was applied to the DSCG-coupled PAHA column and to nonderivate control column. The lysates were allowed to absorb for 24 hours at 4° C. Later the columns were washed with 100-column volumes of Tyrode containing 0.1% NP-40, until no radioactivity could be detected in the washings. The columns were then eluted either with 3-column volumes 10 mM DSCG in Tyrode containing 0.1% NP-40 or with 3-column volumes 10 mM EDTA in 50 mM ammonium bicarbonate, 0.1% NP-40. Significantly higher amounts of iodinated protein were eluted by 10 mM EDTA (11,000 cpm) or 10 mM DSCG (8,000 cpm) from the DSCG-substituted column compared with amount of iodinated protein eluted under the same conditions from the nonderivatized control column (2500 cpm and 1800 cpm, respectively). This indicates the specificity of the eluted product for DSCG. The EDTA eluates were concentrated 20-fold in ultra-thimbles and a sample was applied to SDS-PAGE.

A single band of $60 \times 10^3$ daltons was observed migrating similarly to the immuoprecipitated protein (FIG. 1, lane F). The sample was run in IEF- and the Pi found was 3.9.

EXAMPLE 3

Preparative Isolation of the DSCG-binding Protein

Step A: Tumor Cells

Rat basophile cells (RB1-2H3) were grown in stationary flask culture, as described in Example 1 Step D. Intraperitoneal tumors were grown in 2 weeks old WF/Mai Wistar-Furth rats by injecting 0.5 ml of suspension of 0.4 g of tumor cells/ml of tissue culture medium through a 23-guage needle. Each animal yielded 2-3 g of tumor. The tumors were generally free of necrosis or fatty infiltration and were easily excised.

Step B: Conjugation of DSCG with $^{131}$I-BSA-DNP$_8$

Crystallized bovine serum albumin (BSA) was purchased from Sigma Chemical Company, St. Louis, Miss. U.S.A. DNP$_8$-BSA was prepared according to Eisen [J. Biol. Chem., 254, 7691, (1968)]. Subscripts refer to the number of moles of DNP per mole of BSA. Chloramine-T radioiodination ($^{131}$I) of DNP$_8$-BSA was performed as described by Greenwood et al. [Biochem. J., 89, 114 (1963)].

Conjugation of DSCG to $^{131}$I-labeled DNP$_8$-BSA was carried out as previously described. The unreacted reagent was removed by gel filtration on a sephadox G-25 column. The amount of bound DSCG was determined spectrophotometrically and found to be 4-5 molecules of DSCG per molecule of DNP$_8$-BSA.

Step C: MOPC-315 protein

Mildly reduced and alkylated protein 315 was prepared from the ascitic fluid of Balb/c mice bearing the MOPC-315 tumor, according to Gaetzl and Metzger [Biochemistry, 9, 1167, (1970)]. The protein was affinity purified on a -N-DNP-lysine Sepharose column following the procedure of Inbar et al. [J. Biol. Chem., 246, 6272-6275 (1976)]. The affinity of MOPC-315 myeloma protein to DNP was found to be $2 \times 10^6$ M$^{-1}$ at 25° C.

Step D: Anti-DNP Affinity Column Preparation

Sepharose 4B (Pharmacia) was activated using cyanogen bromide as described by Cuatrecasas [J. Biol. Chem., 945, 3059 (1970)]. Two volumes of packed Sepharose beads were resuspended in one volume of 0.1 M NaHCO$_3$, pH 8.6 and one volume of a 10 mg/ml solution of purified MOPC-315 myeloma protein. After continuous slow stirring at 4° C. for 24 hours the coupling efficiency was 80-90%. The immunoadsorbent was washed with a BBS-Ca$^{2+}$ buffer containing 0.2 M borate, 0.15 M NaCl, 2 mM CaCl$_2$, pH 7.4, on a sintered glass funnel to remove unreacted protein, and resuspended in one volume of 0.1 M ethanol amine, pH 8.5 at 4° C. for one hour to block unreacted iminocarbonate groups, then washed with BBS-Ca$^{2+}$ buffer and stored at 4° C. in BBS-Ca$^{2+}$ buffer, 0.1% sodium azide. Immediately before use, immunoadsorbent was washed with BBS-Ca$^{2+}$ buffer, containing 0.25% Triton X-100.

Step E: Isolation of DSCG-binding Protein

Tumors were cut into large pieces and converted into an acetone powder by the method of Hudgin et al, [J. Biol. Chem., 249, 5536-5543 (1974)]. About 17 g of acetone powder were routinely derived from 100 g net weight of tumor. The powder was stirred for 30 minutes in 40 volumes of PBS and centrifuged at $19,000 \times g$ for 10 minutes. The supernatant was discarded and this step was repeated twice first with the same buffer and then with distilled water. The pellet was blended in 50 volume of PBS containing 0.5% Triton X-100 (scintillation grade, Research Products Corp.). This last extract was centrifuged for 60 minutes at $19,000 \times g$. The supernatant was recovered and diluted in BBS so that the final concentration of Triton was 0.25%.

A sample of the extract was assessed for its DSCG-binding capacity and an excess amount of haptened-iodinated BSA-DSCG was then added to the main preparation. The centrifuged detergent pellet of the washed acetone powder containing about 10% of the protein found in a simple detergent extract of the whole tumors and 30% of the original DSCG binding (Table II). At this point, a preparation of solubilized cells which had been surface-iodinated with $^{125}$I and reacted with haptenated $^{131}$I-BSA-DNP-DSCG was added to the main preparation. This was done exceptionally in order to assess various methods during the development stage of this project The solution was passed through a column containing nonderivatized Sepharose 6B (0.05 ml/ml of solution) in order to absorb any potential nonspecifically adherent materials. The column was attached to the anti-hapten coulumn, the binding capacity of which exceeded the amount of haptenated DSCG-BSA in the preparation by about 25%. In general this amounts to a 1 ml column/25 ml of solution. Both columns were equilibrated with BBS-Ca$^{2+}$ containing 0.25% Triton X-100. After filtration of the preparation through both columns, the affinity column was disengaged from the prefiltration colums and washed with 50 to 100 volumes of BBS-Ca$^{2+}$ containing 0.25% detergent.

The column-bound haptenated BSA-DSCG (in the form of free conjugates and protein-bound conjugate) was eluted with 10$^{-2}$M dinitrophenolate or 10 mM EDTA in PBS-Ca$^{2-}$, 0.25% Triton X-100. Two eluates were collected, each of them after incubation with 1 column volume of hapten or EDTA solutoin for 12 to 18 hours at 4° C. When samples derived from column chromatography in BBS, 0.25% Triton X-100, 10 mM EDTA, were to be analyzed by electrophoresis or for amino acid composition, fractions were concentrated 20 fold on Ultrathinble device (Schleicher & Schull), using a 25,000 daltons cut off membrane. Losses due to binding to the membrane ranged from 5 to 15% and averaged 10%. The preparation then was dialysed in the same membrane bag $Ca^{2+}$ BBS 0.25% Triton X-100 in order to remove the EDTA.

Protein concentrations of solutions containing detergent (Triton) were measured according to the method of Peterson [Anal. Biochem. 83, 346, (1977)]. Polyacrylamide gel electrohporesis was run in SDS buffer according to Laemmli [Nature, 227, 680 (1970)], and 7-15% gradient gels were used. Standards were reduced with 2-mercaptoethanol (0.2 M) before application to the gels. The 60,000 daltons protein detected appears identical to the one previously characterized as the DSCG-binding protein by immunoprecipitation and affinity chromatography techniques of surface labeled basophile cells In this Example there is described a preparative scale method for the purification of the DSCG-binding membranal protein. Starting from intraperitoneal, RBL induced solid tumors, extracts in 0.25% Triton X-100, mixed with lysates of surface labeled RBL-2H3 cells, were reacted with haptenated $^{131}$I-DSCG-BSA conjugate, then passed through an anti-hapten affinity column. The DNP-BSA-$^{131}$I conjugate forms a ternary complex with the DSCG-binding protein via $Ca^{2+}$ as summarized schematically in FIG. 2. This ternary complex is absorbed on the anti-DNP immuno affinity column. Stripping the affinity column from the $^{125}$I-DSCG-binding protein was carried out by the $Ca^{2+}$ chelating agent, EDTA. Purity of the material eluted was checked by $^{131}$I radioactivity accompanying it. When $^{131}$I were detected in the eluant, repetitive affinity chromatography was performed. The overall yield by this method is 10-15% if we compare the amounts of $^{131}$I-DSCG conjugate bound by the detergent extract of the whole tumors and in the final eluage by DNP-OH (Table II). Tumors from 30-40 weanling rats (4-5 litters) allow as to prepare 7 mmoles protein.

TABLE II

YIELD OF ACTIVE DSCG-BINDING PROTEIN DURING PURIFICATION BY AFFINITY CHROMATOGRAPHY

| | | Yield %[a] | |
|---|---|---|---|
| Step | Procedure | Overall | at each step[b] |
| 1 | Acetone powder extract | 29[c] | 29 (4) |
| 2 | Affinity chromatography of complexes | 20 | 70-8 (3)[d] |
| 3 | Gel filtration of complexes | 16 | 80-5 (3) |
| 4 | Dissociation of complexes by EDTA and repetitive affinity chromatography | 14 | 90-5 (3) |

[a]Values are - 1 S.D.
[b]The numbers in the parentheses give the number of results from separate experiments, which were averaged to generate the data shown.
[c]Compared to maximum $^{131}$I-DSCG-BSA-DNP binding capacity found in Triton X-100 extracts of whole tumors. In two of the experiments a direct comparison was made by dividing a single batch of coarsely chopped tumors into two portions. In the other experiments the yield in the acetone powder is relative to the average yield from detergent extracts from separate tumor batches.
[d]Based on the results with 0.01 M 2-4 dinitrophenol as the eluting hapten.

EXAMPLE 4

Preparation of Hetero-Antibodies Against CBP

Rabbits were immunized by multisite intradermal injections of 0.5 mg affinity chromatograph purified DSCG receptor protein per rabbit. in complete Freund's adjuvant. Rabbits were boosted three weeks later with 0.4 mg purified protein and bled 4 and 5 weeks after immunization The serum was separated and stored frozen.

EXAMPLE 5

Monoclonal Antibodies Against Purified DSCG-Binding Protein

Monoclonal antibodies against the purified "protein" were obtained utilizing commonly used techniques [G. Galtre et al, Nature, 266, 550. (1970)].

Spleen cells of $C_{57}Bl/6J$ (female) mice, previously immunized with the purified protein (50 μg/mouse), were fused to the NS1-Ag4/1 myeloma line, in presence of polyethylene glycol 1500. Hybrid clones were screened for Ig secretion and inhibition of DSCG binding to RBL-2H3 cells. Positive hybrid cultures were cloned in soft agar, clones cultured and screened once more for Ig secretions and inhibitions of DSCG binding.

One of the positive hybrid clones obtained in NR-253-11, secreting the $IgG_2b$ monoclonal antibodies against the DSCG-binding protein.

EXAMPLE 6

Blocking of Allergic Response, In-vitro by Means of Anti-DSCG-Binding Protein Antibodies Histamine release for RBL-2H3 cells is an in-vitro analogue of the immediate hypersensitivity reaction and a model system for exocytosis.

It was found that the above antibodies (hetrerogeneous and monoclonal, in the range of 10 μg-0.10 μg) inhibit more than 90% of immunologically mediated histamine release from the RBL-2H3 cells (as tested by the fluorimetric method according to Shore [J. Pharmacol. Exp. Ther., 127, 182 (1959)] and by $^3$H-Serotonin secretion.

Figure 1:
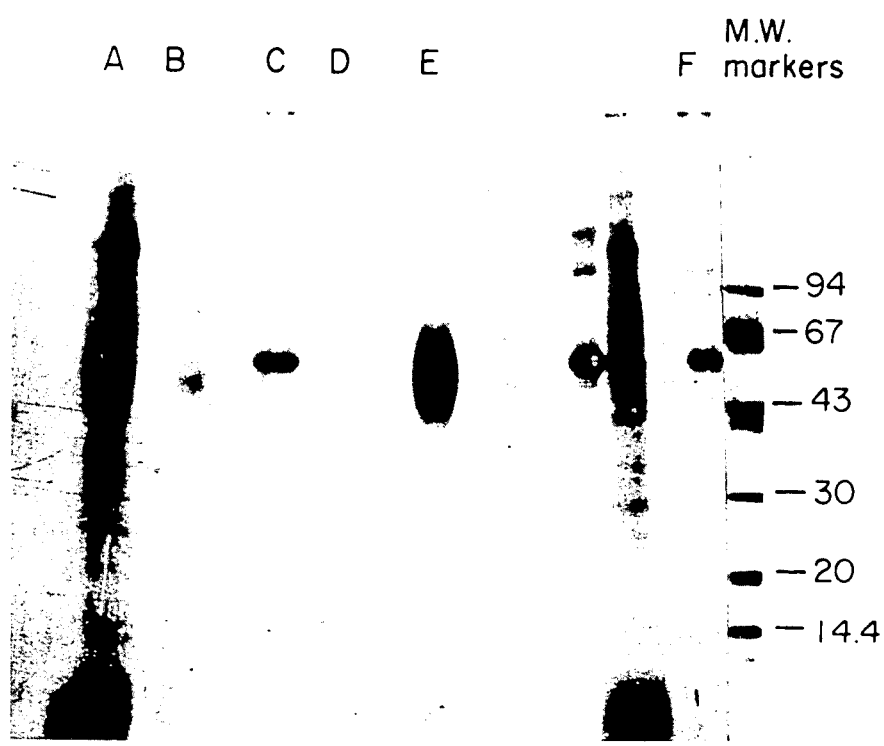
FIG. 1 illustrates an autoradiogram of SDS-PAGE patterns of immunoprecipitates from radiolabeled lysates of RBL-2H3 cells, under nonreducing conditions. Lane A illustrates total lysates of RBL-2H3; Lane B, D illustrate lysozyme-antilysozyme clearing precipitate; Lane C illustrate specific anti-DSCG precipitate; Lane E illustrates specific anti-mouse IgE precipitate; and Lane F illustrates DSCG-building protein obtained by affinity chromatography. Electrophoresis was carried out on a 7-20% gradient gel.
Figure 2:
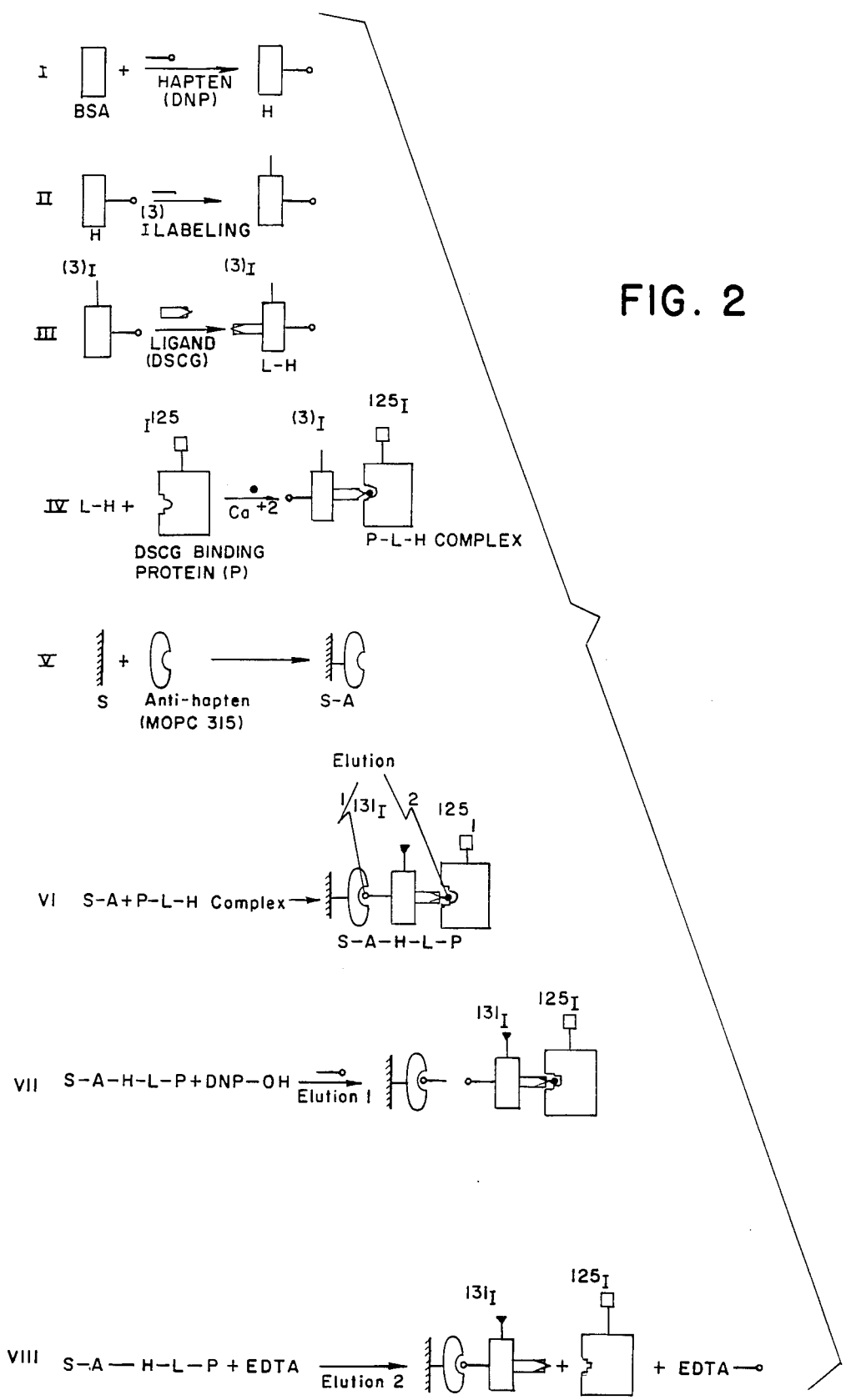
FIG. 2 is a schematic representation of the DSCG-binding protein isolation procedure. H: BSA (DNP)$_8$, L-H: $^{1131}$I-(DSCG)$_4$-BSA-(DNP)$_8$, P-L-H: DSCG-binding protein * conjugate complex; S: Sepharose 4B; S-A: Anti-DNP affinity colum; S-A-H-L-P: DSCG-binding protein * conjugate complex bound to the anti-DNP affinity column.

We claim:

1. An essentially pure protein consisting essentially of the protein, (CBP) , present in nature in membranes of basophile cells and in mast cells, having a molecular weight of about 60,000±2,000 determined by SDS polyacrylamide electrophoresis an isoelectric point of about 3.9 and an amino acid composition of about 4 units of asparagine, 3 units of threonine and serine, 3 units glycine, 2 units alanine, 2 units proline, 1 unit cysteine, 2 units valine, 1 unit methionine, 1 unit isoleucine, 2 units leucine, 1 unit tyrosine, 1 unit phenylalanine, 2 units histamine, 2 units lysine and 1 unit arginine, said protein being able to build calcium and having a calcium dependent affinity to the disodium salt of 1,2 bis(-2 carboxychromon-5-yloxy)-2-hydroxy propane (DSCG).

2. A process for the prepartion of a protein (CBP) present in nature in membranes of basophile cells and in mast cells and capable of binding calcium and having a calcium dependent affinity to the disodium salt of 1,2-bis(-2 carboxychromon-5-yloxy)-2 hydroxy propane (DSCG), comprising:
  binding a cell line having the protein CBP naturally occurring therein with a covalent polyvalent conjugate of a protein and DSCG;
  solubilizing the cell membrane with a non-ionic detergent, resulting in a lysate;
  adding to the lysate antibodies specific for DSCG, resulting in the precipitation of CBP;
  dissolving the precipitate; and
  separating the CBP.

3. A process for the preparation of a protein (CBP) present in nature in membranes of basophile cells and mast cells and capable of binding calcium and having a calcium dependent affinity to the disodium salt of 1,2- bis(-2 carboxychromon-5-yloxy)-2 hydroxy propane (DSCG), comprising:
  solubilizing the membrane of a cell line having the protein CBP naturally occuring therein with a non-ionic detergent, resulting in a lysate;
  preparing an affinity column of DSCG linked by 2-hydroxy-propane moieties to an insoluble matrix;
  absorbing the CBP from the cell lysate onto the column; and
  eluting the CBP from the column.

4. A process for the preparation of a protein (CBP) present in nature in membranes of basophile cells and mast cells and capable of binding calcium and having a calcium dependent affinity to the disodium salt of 1,2- bis(-2 carboxychromon-5-yloxy)-2-hydroxy propane (DSCG), comprising:
  cultivating a cell line having the protein CBP natural ocurring therin;
  extracting, by lysis or by means of an acetone extract, the proteins of such cell line;
  reacting same with a conjugate of another protein with DSCG, and a suitable hapten;
  absorbing the resultant complex on a suitable column comprising a matrix derivatized with antibodies specific to the hapten; and
  eluting the CBP with free hapten or with a calcium-chelating agent.

5. A process according to claim 2, wherein the protein used is bovine serum albumin.

6. A process according to claim 3, wherein the elution is effected by DSCG.

7. A process accordign to claim 3, wherein the elution is effected by calcium-chelating agent.

8. A process according to claim 4, wherein the hapten is DNP.

9. A process according to claim 4 or 8, wherein the other protein is BSA.

10. A method for the blocking of histamine release from mast cells or basephiles, which comprises treating same with anti-CBP-antibodies.

11. A process according with claim 2 wherein said separating step is accomplished by means of gel electrophoresis.

12. The essentially pure protein CBP obtained by the process of any one of claims 2, 3, or 4.

13. A process in accordance with any one of claims 2, 3, or 4 wherein said cell line is a basophile or mast cell line.

14. A process in accordance with claim 4, wherein said extracting step comprises obtaining a lysate by solubilizing with a non-ionic detergent.

15. Antibodies which specifically react with the CBP in accordance with claim 1.

* * * * *